United States Patent [19]

Coombes

[11] Patent Number: 4,917,689
[45] Date of Patent: Apr. 17, 1990

[54] OSTOMY BAG WITH SUPPORT RING

[75] Inventor: Glyn J. A. Coombes, Kemptown, England

[73] Assignee: Smiths Industries Public Limited Company, London, England

[21] Appl. No.: 278,981

[22] Filed: Dec. 2, 1988

[30] Foreign Application Priority Data

Dec. 19, 1987 [GB] United Kingdom ............. 8729637

[51] Int. Cl.4 .................................................. A61F 5/44
[52] U.S. Cl. ............................................................ 604/338
[58] Field of Search ............................ 604/332–345, 604/277

[56] References Cited

U.S. PATENT DOCUMENTS 2,584,540  2/1952  Botvin et al. .................. 604/342
3,351,061 11/1967  Nolan ............................. 604/336
3,780,739 12/1973  Frank ............................. 604/335

FOREIGN PATENT DOCUMENTS 2185404  7/1987  United Kingdom ............. 604/332

Primary Examiner—Jerome L. Kruter
Attorney, Agent, or Firm—Pollock, VandeSande and Priddy

[57] ABSTRACT

An ostomy bg of a wc disposable material has a multi-layer wall with an opening that is secured in register with the patient's stoma by means of a flange. The flange comprises an internal ring and an external ring secured together around the opening. The internal ring has an adhesive front surface secured to the inner surface of the wall around and overlapping the opening. The external ring is of an adhesive material with a backing sheet on its rear side which prevents the external ring adhering to the front of the wall. The external ring overlaps the opening and is exposed by the backing sheet within the opening so that it adheres to the internal ring and protects the edge of the bag opening from body waste material.

7 Claims, 2 Drawing Sheets

OSTOMY BAG WITH SUPPORT RING

BACKGROUND OF THE INVENTION

This invention relates to collection bags.

The invention is more particularly concerned with collection bags, such as ostomy bags for use in collecting discharged body material.

Conventional bags are formed from two flexible sheets of plastics material that are welded together around their edge, one of the sheets having an opening that, in use, is applied about the body stoma so that discharged material enters the bag through the opening. The bag is attached to the patient's skin by means of a flexible adhesive flange that is secured to the bag around the opening, on the outer face of the bag. Some bags additionally have a semi-rigid moulded ring that extends around the bag opening and to which the adhesive flange is attached.

With some bags it can be difficult to attach a flange securely to the material of the bag walls. Where bags are made of a laminate material with a water soluble outer layer it may be necessary to protect the soluble material, around the opening, from body waste products passing through the opening. This can be difficult to achieve. Moulded semi-rigid rings add to the thickness of the bag, can be uncomfortable and increase the cost of assembly of the bag.

BRIEF SUMMARY OF THE INVENTION

It is an object of the present invention to provide a collection bag that can be used to alleviate these difficulties.

According to one aspect of the present invention there is provided a body discharge collection bag formed substantially of flexible material and having a wall with an opening therein that is adapted to be located in register with a body discharge opening, the bag having a first flexible sheet member secured to the inner surface of the wall around the opening and overlapping the opening, the first sheet member having an aperture therein aligned with the opening, a second sheet member being located on the outer surface of the wall and secured to the first sheet member where it overlaps the opening, the second sheet member having an aperture therein aligned with the aperture in the first sheet member, and the outer surface of the second sheet member being adapted for securing the bag to the patient around the body discharge opening such that discharge material enters the bag through the apertures in the first and second sheet members and the bag opening. The outer surface of the second sheet member may be adhesive. The second sheet member may be secured to the first sheet member by means of adhesive where they overlap the opening.

The second sheet member is preferably unattached to the outer surface of the wall. The second sheet member may be of an adhesive material and have a backing sheet attached thereto on the side adjacent the wall such as to prevent adhesion of the second sheet member to the outer surface of the wall, the backing sheet leaving exposed a central region of the second sheet member within the opening of the wall that is adhesively secured to the first sheet member.

The first sheet member may be secured to the wall of the bag by means of adhesive and the front surface of the first sheet member may be adhesive. Alternatively, the second sheet member may be secured to the first sheet member by welding where they overlap the opening.

The wall of the bag is preferably of a wc disposable material. The wall of the bag may have an outer layer of a water soluble material and an inner layer that is water resistant. The outer layer may be of a material including cold-water soluble polyvinyl alcohol. The first and second sheet members may be circular rings.

An ostomy bag according to the present invention, will now be described, by way of example, with reference to the accompanying drawings.

DETAILED DESCRIPTION

Figure 1:
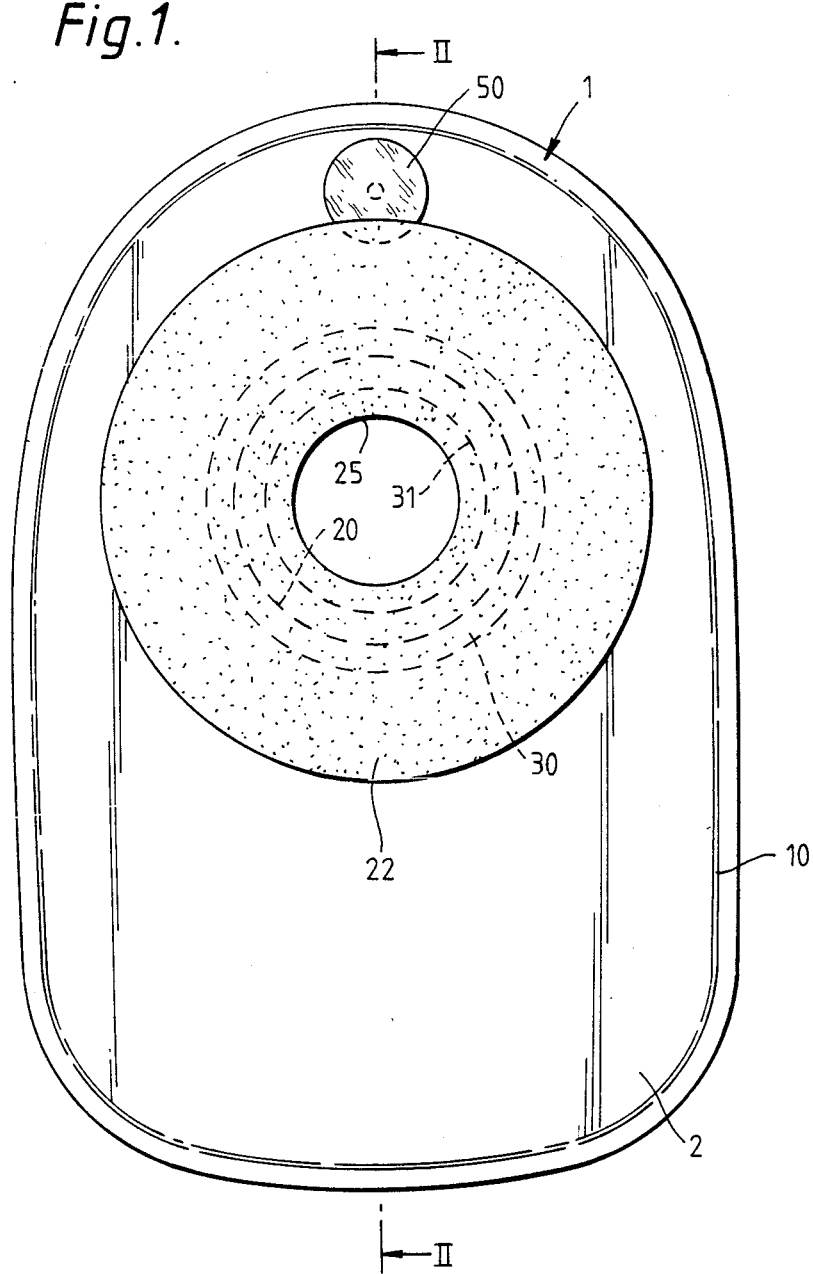
FIG. 1 is a front elevation view of the bag.
Figure 2:
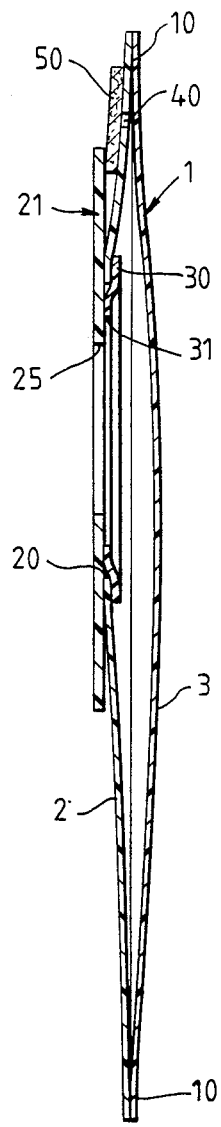
FIG. 2 is a sectional side elevation of the bag along the line II—II of FIG. 1.
Figure 3:
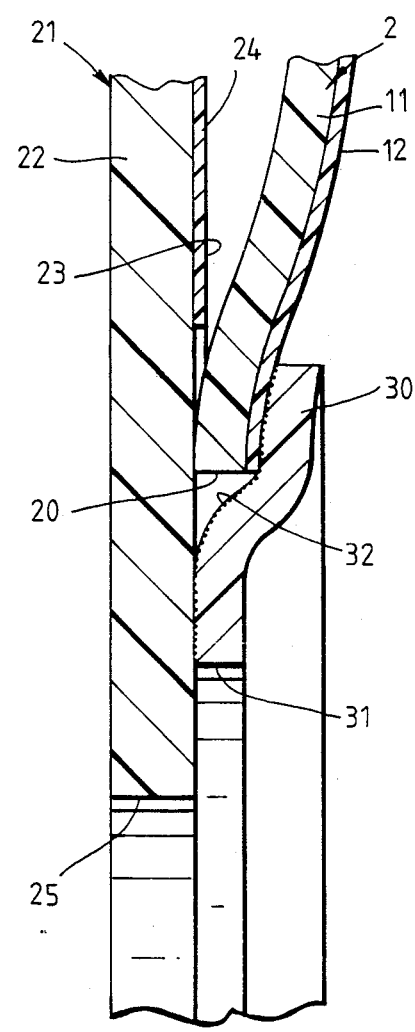
FIG. 3 is an enlarged sectional view of a part of the bag.

The ostomy bag wc disposable and 1 of generally oblong shape formed by sealing two flexible sheets 2 and 3 together around their edge 10. A circular aperture 20 is formed in the front sheet 2, to provide an opening for the bag. A smaller vent 40, about 2 mm in diameter, is formed close to the top of the bag to allow for the escape of gas. The bag also has a filter 50 over the vent 40 to reduce odour from escaping flatus. As so far described, the bag is entirely conventional.

The sheets 2 and 3 are both of the same material, being made of two layers or films 11 and 12. One film 11 is of a cold-water soluble polyvinyl alcohol containing about 12% by weight glycerol; the other film 12 is thinner, being resistant to water and the discharged body waste material and may be, for example, polyvinylidene chloride. The two sheets 2 and 3 are secured together in such a way that the impermeable film 12 provides the inner surface of the bag, while the polyvinyl alcohol film 11 is exposed on the outer surface of the bag. The inner film 12 is relatively impermeable to gases and provides an effective odor barrier.

The bag 1 includes a circular flange or ring 21 which is used to secure the bag to the patient's skin around the ostomy so that the aperture 20 is in register with the stoma. The ring comprises a flexible annular adhesive sheet member 22 of SEEL-A-PEEL (a Registered Trade mark of Eschmann Bros. & Walsh Ltd., the composition of SEEL-A-PEEL is described in GB 2046764B) with an external diameter of about 110 mm and a central aperture of between about 20 mm and 60 mm depending on the size of the stoma. The rear side 23 of the ring 21 is covered over at least its outer edge by a non-adhesive backing sheet 24. The aperture 25 in the ring 21 is aligned with the aperture 20 in the sheet 2, but is smaller than the sheet aperture so that the ring 21 overlaps the bag opening 20. The backing sheet 24 preferably covers the entire rear side 23 of the ring 21 that can contact the sheet 2, leaving exposed only on central region within the opening 20. In this way, there is the direct adhesion between the ring 21 and the outer layer 11 of the sheet 2. This is an advantage if the interply adhesion between the two layers 11 and 12 in the sheet 2 is weak, since the ring 21 is unattached to the layer 11 and will not apply any force tending to separate the two layers.

A second flexible sheet member or ring 30 is secured around the bag opening 20 on the inside surface of the sheet 2. The ring 30 has an outer diameter that is larger than the opening 20 and a central aperture 31 that is smaller than the bag opening, but larger than the aperture 25 in the outer ring 21. The internal ring 30 has an adhesive front surface 32, its aperture 31 being aligned with the opening 20 in the bag and the aperture 25 in the external ring 21. In this way, the internal ring 30 overlaps the bag opening 20 and is adhesively secured to the rear surface of the external ring 21.

The external ring 21 and internal ring 30 are thereby joined together around the opening 20 of the bag so as to protect the edge of the water soluble layer 11 wherein it is exposed around the opening 20. This serves to prevent discharged body waste material that enters the bag from coming into contact with the water soluble layer 11.

Assembly of the ring 21 on the bag 1 is relatively simple. The external ring 21 and internal ring 30 may, prior to assembly, be in the form of discs, without the central apertures 25 and 31. During assembly, the two discs are placed on opposite sides of the sheet 2, over the aperture 20, prior to the sheets 2 and 3 being joined together. The two discs are joined together by pressing where they overlap the aperture. A hole can then be punched through both discs at the same time and the sheet 3 subsequently welded to the sheet 2. This form of assembly would make the apertures 25 and 31 in the external and internal rings be of the same diameter.

Other assembly techniques are possible in which the rings are assembled after joining the two sheets 2 and 3 together. The two rings could be joined together prior to assembling on the bag opening.

The inner and outer rings could be made of any flexible sheet member and could be joined together around the bag opening in other ways, such as by welding. The external ring need not itself be of an adhesive material, but could be secured to the patient's body by means of a separate intermediate peristomal wafer of adhesive material.

The invention is not confined to use with wc disposable bags, but could be used with non-disposable bags.

By using two flexible sheet members sandwiched together about the bag opening, a secure assembly is produced which can be of small thickness and good flexibility to ensure comfort to the wearer. The present contruction also helps alleviate the difficulties that arise where the nature of the external surface of the bag reduces adhesion by the flange to the surface and where there is low interply adhesion between layers in a multi-layer bag wall.

What I claim is:

1. A body discharge collection bag comprising: a first wall of flexible material; a second wall of flexible material joined with the first wall around its edge, the second wall having a opening therein for location in register with a body discharge opening so that body discharge material can enter the bag through the opening; a first flexible sheet member having an aperture therein smaller than said opening; means securing the first sheet member to the inner surface of the second wall with the aperture in alignment with and overlapping the opening; a second flexible sheet member having an aperture therein smaller than said opening, said second sheet member being adapted to secure the bag to the patient around the body discharge opening; and means securing the second sheet member to the first sheet member where said first sheet member overlaps the opening, with the aperture in the second sheet member in alignment with the aperture in the first sheet member and with the second sheet member being located on the outer surface of the second wall so that body discharge material enters the bag through the apertures in the first and second sheet members without contacting the second wall around its opening.

2. A body discharge collection bag according to claim 1, wherein the second sheet member is adapted to secure the bag to the patient by an adhesive outer surface on the second sheet member.

3. A body discharge collection bag according to claim 1, wherein the said means securing the second sheet member to the first sheet member is adhesive means.

4. A body discharge collection bag according to claim 1, wherein the said second sheet member is unattached to the outer surface of the second wall.

5. A body discharge collection bag according to claim 4, wherein the said second sheet member is of an adhesive material, wherein the bag includes a non-adhesive backing sheet attached to said second sheet member on the side adjacent the second wall such as to prevent adhesion of the second sheet member to the outer surface of the second wall, the backing sheet being dimensioned to leave exposed a central region of the second sheet member within the opening of the second wall, said central region being adhesively secured to the first sheet member.

6. A body discharge collection bag according to claim 1, wherein the said means securing the first sheet member to the inner surface of the wall is adhesive means.

7. A body discharge collection bag according to claim 1, wherein the said first sheet member has a front surface of an adhesive material. member being adhered to the first sheet member where said first sheet member overlaps the opening, with the aperture in the second sheet member in alignment with the aperture in the first sheet member; and a non-adhesive backing sheet attached to said second sheet member on the side adjacent the second wall such as to prevent adhesion of the second sheet member to the outer surface of the second wall but to leave exposed a central region of the second sheet member within the opening of the second wall which central region is adhesively secured to the first sheet member so that body discharge material enters the bag through the apertures in the first and second sheet members without contacting the second wall around its opening.

* * * * *